(12) United States Patent
Widdowson et al.

(10) Patent No.: US 6,297,265 B2
(45) Date of Patent: Oct. 2, 2001

(54) BENZOISOTHIAZOLE-SUBSTITUTED COMPOUNDS USEFUL AS IL-8 RECEPTOR ANTAGONISTS

(75) Inventors: Katherine L. Widdowson, King of Prussia; Hong Nie, Conshohocken, both of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/508,039

(22) PCT Filed: Sep. 4, 1998

(86) PCT No.: PCT/US98/18569

§ 371 Date: Mar. 3, 2000

§ 102(e) Date: Mar. 3, 2000

(87) PCT Pub. No.: WO99/11264

PCT Pub. Date: Mar. 11, 1999

Related U.S. Application Data

(60) Provisional application No. 60/057,998, filed on Sep. 5, 1997.

(51) Int. Cl.$^7$ ............... A61K 31/428; C07D 275/06; C07D 513/04
(52) U.S. Cl. ............... 514/367; 514/373; 548/159; 548/207
(58) Field of Search ............... 548/159, 207; 514/367, 373

(56) References Cited

U.S. PATENT DOCUMENTS

| | | | |
|---|---|---|---|
| 5,929,250 | * | 7/1999 | Widdowson et al. ............ 548/361.1 |
| 6,015,908 | * | 1/2000 | Widdowson et al. ............ 548/207 |
| 6,043,374 | * | 3/2000 | Widdowson et al. ............ 548/207 |

FOREIGN PATENT DOCUMENTS

WO 95/33746    12/1995    (WO).

OTHER PUBLICATIONS

Chiarino, et al. 1,2–Benzisothiazole 2,2–Dioxide and Derivatives. Journal of Heterocyclic Chemistry. Nov.–Dec. 1986, vol. 23, No. 6, pp. 1645–1649, especially p. 1646, Table I.

* cited by examiner

*Primary Examiner*—Laura L. Stockton
(74) *Attorney, Agent, or Firm*—Soma G. Simon; Dara L. Dinner; Charles M. Kinzig

(57) ABSTRACT

This invention relates to novel benzoisothiazole substituted compounds, pharmaceutical compositions, processes for their preparation, and use thereof in treating IL-8, GROα, GROβ, GROγ, ENA-78 and NAP-2 mediated diseases.

14 Claims, No Drawings

BENZOISOTHIAZOLE-SUBSTITUTED COMPOUNDS USEFUL AS IL-8 RECEPTOR ANTAGONISTS

This application is a 371 of PCT/US 98/18569 filed Sep. 4, 1998 which claims the benefit of U.S. Provisional application Ser. No. 60/057,998 filed Sep. 5, 1997.

FIELD OF THE INVENTION

This invention relates to novel benzoisothiazole substituted compounds, pharmaceutical compositions, processes for their preparation, and use thereof in treating IL-8, GROα, GROβ, GROγ, ENA-78 and NAP-2 mediated diseases.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP. M. Baggiolini et al., *J. Clin. Invest.* 84, 1045 (1989); J. Schroder et al., *J. Immunol.* 139, 3474 (1987) and *J. Immunol.* 144, 2223 (1990); Strieter, et al., *Science* 243, 1467 (1989) and *J. Biol. Chem.* 264, 10621 (1989); Cassatella et al., *J. Immunol.* 148, 3216 (1992).

GROα, GROβ, GROγ and NAP-2 also belong to the chemokine α family. Like IL-8 these chemokines have also been referred to by different names. For instance GROα, β, γ have been referred to as MGSAα, β and γ respectively (Melanoma Growth Stimulating Activity), see Richmond et al., J. Cell Physiology 129, 375 (1986) and Chang et al., *J. Immunol* 148, 451 (1992). All of the chemokines of the α-family which possess the ELR motif directly preceding the CXC motif bind to the IL-8 B receptor.

IL-8, GROα, GROβ, GROγ, NAP-2 and ENA-78 stimulate a number of functions in vitro. They have all been shown to have chemoattractant properties for neutrophils, while IL-8 and GROα have demonstrated T-lymphocytes, and basophiles chemotactic activity. In addition IL-8 can induce histamine release from basophils from both normal and atopic individuals GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, Groα, GROβ, GROγ and NAP-2 promote the accumulation and activation of neutrophils, these chemokines have been implicated in a wide range of acute and chronic inflammatory disorders including psoriasis and rheumatoid arthritis, Baggiolini et al., *FEBS Lett.* 307, 97 (1992); Miller et al., *Crit. Rev. Immunol.* 12, 17 (1992); Oppenheim et al., *Annu. Rev. Immunol.* 9, 617 (1991); Seitz et al., *J. Clin. Invest.* 87, 463 (1991); Miller et al., *Am. Rev. Respir. Dis.* 146, 427 (1992); Donnely et al., *Lancet* 341, 643 (1993). In addition the ELR chemokines (those containing the amino acids ELR motif just prior to the CXC motif) have also been implicated in angiostasis. Strieter et al., *Science* 258, 1798 (1992).

In vitro, IL-8, GROα, GROβ, GROγ and NAP-2 induce neutrophil shape change, chemotaxis, granule release, and respiratory burst, by binding to and activating receptors of the seven-transmembrane, G-protein-linked family, in particular by binding to IL-8 receptors, most notably the B-receptor. Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research,* Vol.40, pp.33–98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8Rβ, which has high affinity for IL-8 as well as for GRO-α, GROβ, GROγ and NAP-2. See Holmes et al., supra; Murphy et al., *Science* 253, 1280 (1991); Lee et al.,*J. Biol. Chem.* 267, 16283 (1992); LaRosa et al., *J. Biol. Chem.* 267, 25402 (1992); and Gayle et al.,*J. Biol. Chem.* 268, 7283 (1993).

There remains a need for treatment, in this field, for compounds which are capable of binding to the IL-8 α or β receptor. Therefore, conditions associated with an increase in IL-8 production (which is responsible for chemotaxis of neutrophil and T-cells subsets into the inflammatory site) would benefit by compounds which are inhibitors of IL-8 receptor binding.

SUMMARY OF THE INVENTION

This invention provides for a method of treating a chemokine mediated disease, wherein the chemokine is one which binds to an IL-8 α or β receptor and which method comprises administering an effective amount of a compound of Formula (I) or a pharmaceutically acceptable salt thereof. In particular the chemokine is IL-8.

This invention also relates to a method of inhibiting the binding of IL-8 to its receptors in a mammal in need thereof which comprises administering to said mammal an effective amount of a compound of Formula (I).

The present invention also provides for the novel compounds of Formula (I), and pharmaceutical compositions comprising a compound of Formula (I) and a pharmaceutical carrier or diluent.

Compounds of Formula (I) useful in the present invention are represented by the structure:

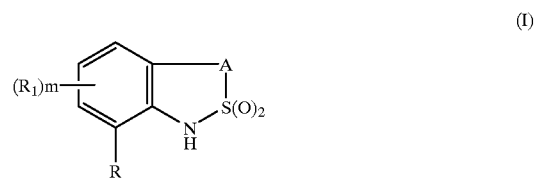

wherein
R is —NH—C(X)—NH—$(CR_{13}R_{14})_v$—Z;
Z is W, optionally substituted heteroaryl, optionally substituted $C_{5-8}$ cycloalkyl, optionally substituted $C_{1-10}$ alkyl, optionally substituted $C_{2-10}$ alkenyl, or an optionally substituted $C_{2-10}$ alkynyl;
X is =O, or =S;
A is $CR_{20}R_{21}$;
$R_1$ is independently selected from hydrogen; halogen; nitro; cyano; halosubstituted C1-10 alkyl; $C_{1-10}$ alkyl;

C$_{2-10}$ alkenyl; C$_{1-10}$ alkoxy; halosubstituted C$_{1-10}$ alkoxy; azide; (CR$_8$R$_8$)qS(O)$_t$R$_4$, hydroxy; hydroxy C$_{1-4}$alkyl; aryl; aryl C$_{1-4}$ alkyl; aryloxy; arylC$_{1-4}$ alkyloxy; heteroaryl; heteroarylalkyl; heterocyclic; heterocyclicC$_{1-4}$alkyl; heteroarylC$_{1-4}$ alkyloxy; arylC$_{2-10}$ alkenyl; heteroarylC$_{2-10}$ alkenyl; heterocyclicC$_{2-10}$ alkenyl; (CR$_8$R$_8$)qNR$_4$R$_5$; C$_{2-10}$alkenylC(O)NR$_4$R$_5$; (CR$_8$R$_8$)qC(O)NR$_4$R$_5$; (CR$_8$R$_8$)qC(O)NR$_4$R$_{10}$; S(O)$_3$H; S(O)$_3$R$_8$; (CR$_8$R$_8$)qC(O)R$_{11}$; C$_{2-10}$ alkenylC(O)R$_{11}$; C$_{2-10}$alkenylC(O)OR$_{11}$; (CR$_8$R$_8$)qC(O)O$_{11}$; (CR$_8$R$_8$)qC(O)OR$_{12}$; (CR$_8$R$_8$)qOC(O)R$_{11}$; (CR$_8$R$_8$) qNR$_4$C(O)R$_{11}$; (CR$_8$R$_8$)qC(NR$_4$)NR4R$_5$; (CR$_8$R$_8$) qNR$_4$C(NR$_5$)R$_{11}$; (CR$_8$R$_8$)qNHS(O)$_2$R$_{17}$; (CR$_8$R$_8$)qS (O)$_2$NR$_4$R$_5$; or two R$_1$ moieties together may form —O—(CH$_2$)$_s$O— or a 5 to 6 membered saturated or unsaturated ring, and wherein the aryl, heteroaryl, and heterocyclic containing rings may be optionally substituted;

n is an integer having a value of 1 to 3;
m is an integer having a value of 1 or 3;
q is 0, or an integer having a value of 1 to 10;
t is 0, or an integer having a value of 1 or 2;
s is an integer having a value of 1 to 3;
v is 0, or an integer having a value of 1 to 4;
R$_4$ and R$_5$ are independently hydrogen, optionally substituted C$_{1-4}$ alkyl, optionally substituted aryl, optionally substituted aryl C$_{1-4}$alkyl, optionally substituted heteroaryl, optionally substituted heteroaryl C$_{1-4}$alkyl, heterocyclic, heterocyclic C$_{1-4}$ alkyl, or R$_4$ and R$_5$ together with the nitrogen to which they are attached form a 5 to 7 member ring which may optionally comprise an additional heteroatom selected from O/N/S;

Y is independently selected from hydrogen; halogen; nitro; cyano; halosubstituted C$_{1-10}$ alkyl; C$_{1-10}$ alkyl; C$_{2-10}$ alkenyl; C$_{1-10}$ alkoxy; halosubstituted C$_{1-10}$ alkoxy; azide; (CR$_8$R$_8$)qS(O)$_t$R$_4$; hydroxy; hydroxyC$_{1-4}$alkyl; aryl; aryl C$_{1-4}$ alkyl; aryloxy; arylC$_{1-4}$ alkyloxy; heteroaryl; heteroarylalkyl; heteroaryl C$_{1-4}$ alkyloxy; heterocyclic, heterocyclicC$_{1-4}$alkyl; aryl C$_{2-10}$ alkenyl; heteroarylC$_{2-10}$ alkenyl; heterocyclicC$_{2-10}$alkenyl; (CR$_8$R$_8$)qNR$_4$R$_5$; C$_{2-10}$alkenylC(O)NR$_4$R$_5$; (CR$_8$R$_8$) qC(O)NR$_4$R$_5$; (CR$_8$R$_8$)qC(O)NR$_4$R$_{10}$; S(O)$_3$H; S(O)$_3$R$_8$; (CR$_8$R$_8$)qC(O)R$_{11}$; C$_{2-10}$ alkenylC(O)R$_{11}$; C$_{2-10}$alkenylC(O)OR$_{11}$; (CR$_8$R$_8$)qC(O)OR$_{11}$; (CR$_8$R$_8$) qC(O)OR$_{12}$; (CR$_8$R$_8$)q OC(O)R$_{11}$; (CR$_8$R$_8$)qNR$_4$C(O) R$_{11}$; (CR$_8$R$_8$)qC(NR$_4$)NR$_4$R$_5$; (CR$_8$R$_8$)q NR$_4$C(NR$_5$) R$_{11}$; (CR$_8$R$_8$)qNHS(O)$_2$R$_{18}$; (CR$_8$R$_8$)qS(O)$_2$NR$_4$R$_5$; or two Y moieties together may form O—(CH$_2$)$_s$—O or a 5 to 6 membered saturated or unsaturated ring, and wherein the aryl, heteroaryl, and heterocyclic containing rings may be optionally substituted;

R$_6$ and R$_7$ are independently hydrogen or a C$_{1-4}$ alkyl group, or R$_6$ and R$_7$ together with the nitrogen to which they are attached form a 5 to 7 member ring which ring may optionally contain an additional heteroatom which heteroatom is selected from oxygen, nitrogen or sulfur;

R$_8$ is independently hydrogen or C$_{1-4}$ alkyl;
R$_{10}$ is C$_{1-10}$ alkyl C(O)$_2$R$_8$;
R$_{11}$ is hydrogen, C$_{1-4}$ alkyl, optionally substituted aryl, optionally substituted aryl C$_{1-4}$alkyl, optionally substituted heteroaryl, optionally substituted heteroarylC$_{1-4}$alkyl, optionally substituted heterocyclic, or optionally substituted heterocyclicC$_{1-4}$alkyl;
R$_{12}$ is hydrogen, C$_{1-10}$ alkyl, optionally substituted aryl or optionally substituted arylalkyl;

R$_{13}$ and R$_{14}$ are independently hydrogen, optionally substituted C$_{1-4}$ alkyl, or one of R$_{13}$ and R$_{14}$ may be an optionally substituted aryl;

R$_{15}$ and R$_{16}$ are independently hydrogen, or an optionally substituted C$_{1-4}$ alkyl;

R$_{17}$ is C$_{1-4}$alkyl, aryl, arylalkyl, heteroaryl, heteroarylC$_{1-4}$alkyl, heterocyclic, or heterocyclicC$_{1-4}$alkyl, wherein the aryl, heteroaryl and heterocyclic rings may all be optionally substituted;

R$_{18}$ is NR$_6$R$_7$, alkyl, arylC$_{1-4}$ alkyl, arylC$_{2-4}$alkenyl, heteroaryl, heteroaryl C$_{1-4}$alkyl, heteroarylC$_{2-4}$ alkenyl, heterocyclic, heterocyclicC$_{1-4}$ alkyl, wherein the aryl, heteroaryl and heterocyclic rings may all be optionally substituted;

R$_{20}$ and R$_{21}$ are independently hydrogen, halogen, cyano, halosubstituted C$_{1-10}$alkyl, C$_{1-10}$alkyl, aryl, aryl C$_{1-4}$ alkyl, heteroaryl; heteroarylalkyl, heterocyclic, heterocyclic C$_{1-4}$alkyl, (CR$_8$R$_8$)qOR$_4$, (CR$_8$R$_8$)qC(O)R$_{11}$, (CR$_8$R$_8$)qC(O)OR$_{11}$, (CR$_8$R$_8$)qC(O)OR$_{12}$, (CR$_8$R$_8$) qOC(O)R$_{11}$, (CR$_8$R$_8$)qNR$_4$R$_5$, (CR$_8$R$_8$)qNR$_4$C(O)R$_{11}$, (CR$_8$R$_8$)qC(O)NR$_4$R$_5$ (CR$_8$R$_8$)qC(O)NR$_4$R$_{10}$, or together R$_{20}$ and R$_{21}$ may form =R$_{22}$; and wherein the aryl, heteroaryl, and heterocyclic containing rings may be optionally substituted; further provided that both R$_{20}$ and R$_{21}$ are not hydrogen;

R$_{22}$ is a C$_{1-4}$ alkyl, aryl, aryl C$_{1-4}$ alkyl, heteroaryl; heteroarylalkyl, heterocyclic, or heterocyclic C$_{1-4}$alkyl, and wherein all of these moieties may be optionally substituted;

W is

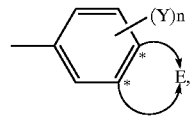

or

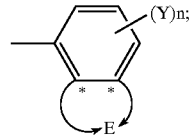

the E containing ring is optionally selected from

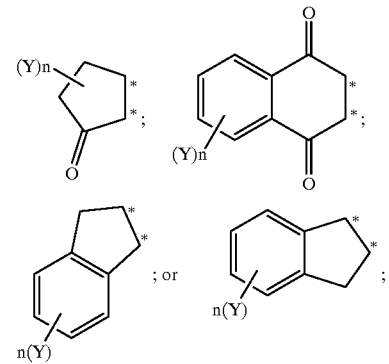

the asterix * denoting point of attachment of the ring;
or a pharmaceutically acceptable salt thereof.

DETAILED DESCRIPTION OF THE INVENTION

The compounds of Formula (I) may also be used in association with the veterinary treatment of mammals, other than humans, in need of inhibition of IL-8 or other chemokines which bind to the EL-8 α and β receptors. Chemokine mediated diseases for treatment, therapeutically or prophylactically, in animals include disease states such as those noted herein in the Methods of Treatment section.

In compounds of Formula (I), suitably $R_1$ is independently selected from hydrogen; halogen; nitro; cyano; halosubstituted $C_{1-10}$ alkyl, such as $CF_3$; $C_{1-10}$ alkyl, such as methyl, ethyl, isopropyl, or n-propyl; $C_{2-10}$ alkenyl; $C_{1-10}$ alkoxy, such as methoxy, or ethoxy; halosubstituted $C_{1-10}$ alkoxy, such as trifluoromethoxy; azide; $(CR_8R_8)qS(O)_tR_4$, wherein t is 0, 1 or 2; hydroxy; hydroxy $C_{1-4}$alkyl, such as methanol or ethanol; aryl, such as phenyl or naphthyl; aryl $C_{1-4}$ alkyl, such as benzyl; aryloxy, such as phenoxy; aryl $C_{1-4}$ alkyloxy, such as benzyloxy; heteroaryl; heteroarylalkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; $(CR_8R_8)qNR_4R_5$; $C_{2-10}$ alkenyl $C(O)NR_4R_5$; $(CR_8R_8)qC(O)NR_4R_5$; $(CR_8R_8)qC(O)NR_4R_{10}$; $S(O)_3H$; $S(O)_3R_8$; $(CR_8R_8)qC(O)R_{11}$; $C_{2-10}$ alkenyl $C(O)R_{11}$; $C_{2-10}$ alkenyl $C(O)OR_{11}$; $(CR_8R_8)qC(O)OR_{11}$; $(CR_8R_8)qC(O)OR_{12}$; $(CR_8R_8)qOC(O)R_{11}$; $(CR_8R_8)qNR_4C(O)R_{11}$; $(CR_8R_8)qC(NR_4)NR_4R_5$; $(CR_8R_8)qNR_4C(NR_5)R_{11}$; $(CR_8R_8)qNHS(O)_2R_{17}$; $(CR_8R_8)qS(O)_2NR_4R_5$; or two $R_1$ moieties together may form $O—(CH_2)_sO—$ or a 5 to 6 membered saturated or unsaturated ring. All of the aryl, heteroaryl, and heterocyclic containing moieties above may be optionally substituted as defined herein below.

Suitably, s is an integer having a value of 1 to 3.

Suitably, q is 0, or an integer having a value of 1 to 10.

It is recognized that the $R_1$ moiety may be substituted on the benzene ring or the A containing ring, if possible, preferably on the benzene ring.

When $R_1$ forms a dioxybridge, s is preferably 1. When $R_1$ forms an additional saturated or unsaturated ring, it is preferably 6 membered unsaturated ring resulting in a naphthalene ring system. These rings may be optionally substituted independently, 1 to 3 times, by other $R_1$ moieties as defined above.

Suitably, $R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from O/N/S.

Suitably, $R_6$ and $R_7$ are independently hydrogen or a $C_{1-4}$ alkyl group, or $R_6$ and $R_7$ together with the nitrogen to which they are attached form a 5 to 7 member ring which ring may optionally contain an additional heteroatom which heteroatom is selected from oxygen, nitrogen or sulfur.

Suitably, $R_8$ is independently hydrogen or $C_{1-4}$ alkyl.

Suitably, $R_{10}$ is $C_{1-10}$ alkyl $C(O)_2R_8$, such as $CH_2C(O)_2H$ or $CH_2C(O)_2CH_3$.

Suitably, $R_{11}$ is hydrogen, $C_{1-4}$ alkyl, aryl, aryl $C_{1-4}$ alkyl, heteroaryl, heteroaryl $C_{1-4}$alkyl, heterocyclic, or heterocyclic $C_{1-4}$alkyl.

Suitably, $R_{12}$ is hydrogen, $C_{1-10}$ alkyl, optionally substituted aryl or optionally substituted arylalkyl.

Suitably, $R_{13}$ and $R_{14}$ are independently hydrogen, an optionally substituted $C_{1-4}$ alkyl which may be straight or branched as defined herein, or one of $R_{13}$ and $R_{14}$ are an optionally substituted aryl; v is 0, or an integer having a value of 1 to 4.

When $R_{13}$ or $R_{14}$ are an optionally substituted alkyl, the alkyl moiety may be substituted one to three times independently by halogen; halosubstituted $C_{1-4}$ alkyl such as trifluoromethyl; hydroxy; hydroxy $C_{1-4}$alkyl, $C_{1-4}$ alkoxy; such as methoxy, or ethoxy, halosubstituted $C_{1-10}$ alkoxy, $S(O)_tR_4$; aryl; $NR_4R_5$; $NHC(O)R_4$; $C(O)NR_4R_5$; or $C(O)OR_8$.

Suitably, $R_{17}$ is $C_{1-4}$alkyl, aryl, arylalkyl, heteroaryl, heteroaryl $C_{1-4}$alkyl, heterocyclic, or heterocyclic$C_{1-4}$alkyl, wherein the aryl, heteroaryl and heterocyclic rings may all be optionally substituted.

Suitably, Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)qS(O)_tR_4$; hydroxy; hydroxy $C_{1-4}$alkyl; aryl; aryl $C_{1-4}$ alkyl; aryloxy; aryl$C_{1-4}$ alkyloxy; heteroaryl; heteroarylalkyl; heteroaryl $C_{1-4}$ alkyloxy; heterocyclic, heterocyclic $C_{1-4}$alkyl; aryl $C_{2-10}$ alkenyl; heteroaryl $C_{2-10}$ alkenyl; heterocyclic $C_{2-10}$ alkenyl; $(CR_8R_8)qNR_4R_5$; $C_{2-10}$ alkenyl $C(O)NR_4R_5$; $(CR_8R_8)qC(O)NR_4R_5$; $(CR_8R_8)qC(O)NR_4R_{10}$; $S(O)_3H$; $S(O)_3R_8$; $(CR_8R_8)qC(O)R_{11}$; $C_{2-10}$ alkenyl $C(O)R_{11}$; $C_{2-10}$ alkenyl $C(O)OR_{11}$; $(CR_8R_8)qC(O)OR_{11}$; $(CR_8R_8)qC(O)OR_{12}$; $(CR_8R_8)qOC(O)R_{11}$; $(CR_8R_8)qNR_4C(O)R_{11}$; $(CR_8R_8)qC(NR_4)NR_4R_5$; $(CR_8R_8)qNR_4C(NR_5)R_{11}$;$(CR_8R_8)qNHS(O)_2R_{18}$; $(CR_8R_8)qS(O)_2NR_4R_5$ or two Y moieties together may form $O—(CH_2)_sO—$ or a 5 to 6 membered saturated or unsaturated ring. The aryl, heteroaryl and heterocyclic moieties noted above may all be optionally substituted as defined herein.

When Y forms a dioxybridge, s is preferably 1. When Y forms an additional saturated or unsaturated ring, it is preferably 6 membered unsaturated ring resulting in a naphthylene ring system. These rings may be optionally substituted 1 to 3 times by other Y moieties as defined above.

Suitably, $R_{18}$ is $NR_6R_7$, alkyl, aryl $C_{1-4}$ alkyl, aryl$C_{2-4}$ alkenyl, heteroaryl, heteroaryl-$C_{1-4}$alkyl, heteroaryl$C_{2-4}$ alkenyl, heterocyclic, heterocyclic$C_{1-4}$ alkyl, wherein the aryl, heteroaryl and heterocyclic rings may all be optionally substituted.

Y is preferably a halogen, $C_{1-4}$ alkoxy, optionally substituted aryl, optionally substituted aryloxy or arylalkoxy, methylenedioxy, $NR_4R_5$, thio $C_{1-4}$alkyl, thioaryl, halosubstituted alkoxy, optionally substituted $C_{1-4}$ alkyl, or hydroxy alkyl. Y is more preferably mono-substituted halogen, disubstituted halogen, mono-substituted alkoxy, disubstituted alkoxy, methylenedioxy, aryl, or alkyl, more preferably these groups are mono or di-substituted in the 2'- position or 2'-, 3'-position.

While Y may be substituted in any of the 5 ring positions, Y is preferably mono-substituted in the 2'-position or 3'-position, with the 4'- preferably being unsubstituted. If the ring is disubstituted, the substituents are preferably in the 2' or 3' position of a monocyclic ring. While both $R_1$ and Y can both be hydrogen, it is preferred that at least one of the rings be substituted, preferably both rings are substituted.

Suitably X is $=O$, or $=S$.

A is suitably $CR_{20}R_{21}$.

Suitably $R_{20}$ and $R_{21}$ are independently hydrogen, halogen, cyano, halosubstituted $C_{1-10}$ alkyl; $C_{1-10}$ alkyl; aryl; aryl $C_{1-4}$ alkyl; heteroaryl; heteroaryl$_{1-4}$ alkyl; heterocyclic, heterocyclic $C_{1-4}$alkyl; $(CR_8R_8)qOR_4$, $(CR_8R_8)qC(O)R_{11}$; $(CR_8R_8)qC(O)OR_{11}$; $(CR_8R_8)qC(O)$ OR$_{12}$; (CR$_8$R$_8$)qOC(O)R$_{11}$; (CR$_8$R$_8$)qNR$_4$R$_5$; (CR$_8$R$_8$)qNR$_4$C(O)R$_{11}$; (CR$_8$R$_8$)qC(O)NR$_4$R$_{10}$; or (CR$_8$R$_8$)qC(O)NR$_4$R$_5$; and wherein the aryl, heteroaryl, and heterocyclic containing rings may be optionally substituted, provided that both R$_{20}$ and R$_{21}$ are not hydrogen; or together R$_{20}$ and R$_{21}$ form a double bond connected to an R22 group, as in =R$_{22}$.

Suitably, R$_{22}$ is a C$_{1-4}$ alkyl, aryl, aryl C$_{1-4}$ alkyl, heteroaryl; heteroarylalkyl, heterocyclic, or heterocyclic C$_{1-4}$alkyl, and wherein all of these moieties may be optionally substituted. Preferably, R$_{20}$ and R$_{21}$ form a methylene group.

Suitably R$_{15}$ and R$_{16}$ are independently hydrogen, or an optionally substituted C$_{1-4}$ alkyl as defined above for R$_{13}$ and R$_{14}$.

In compounds of Formula (I), suitably Z is W, optionally substituted heteroaryl, optionally substituted C$_{5-8}$ cycloalkyl, optionally substituted C$_{1-10}$ alkyl, optionally substituted C$_{2-10}$ alkenyl, or an optionally substituted C$_{2-10}$ alkynyl.

Suitably, W is

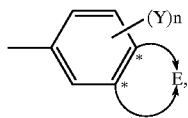

or

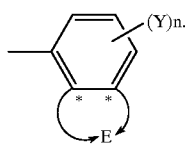

Suitably, the E containing ring is optionally selected from

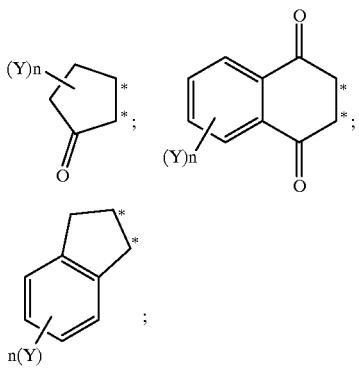

or

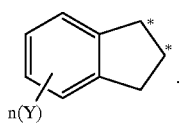

The E containing ring, denoted by its point of attachment through the asterix (*), may optionally be present. If not present, the ring is a phenyl moiety which is substituted by the Y terms as shown. The E ring may be substituted by a (Y)$_n$ moiety in any ring, saturated or unsaturated, and is shown for purposes herein substituted only in the unsaturated ring(s).

When Z is an optionally substituted C$_{5-8}$ cycloalkyl ring, the ring may be optionally substituted by the (Y)$_n$ term as defined above.

When Z is an optionally substituted C$_{1-10}$ alkyl, an optionally substituted C$_{2-10}$ alkenyl, or an optionally substituted C$_{2-10}$ alkynyl moiety, these moieties may be optionally substituted one or more times independently by halogen; nitro; cyano; halosubstituted C$_{1-10}$ alkyl, such as trifluoromethyl; C$_{1-10}$ alkoxy; halosubstituted C$_{1-10}$ alkoxy; S(O)$_t$R$_4$; hydroxy; hydroxy C$_{1-4}$alkyl; aryloxy; arylC$_{1-4}$ alkyloxy; heteroaryloxy; heteroaryl C$_{1-4}$ alkyloxy; heterocyclic, heterocyclic C$_{1-4}$alkyl; heterocyclic-oxy; heterocyclic C$_{1-4}$ alkyloxy; NR$_4$R$_5$; C(O)NR$_4$R$_5$; C(O)NR$_4$R$_{10}$; S(O)$_3$H; S(O)$_3$R$_8$; C(O)R$_{11}$; C(O)OR$_{12}$; OC(O)R$_{11}$; or NR$_4$C(O)R$_{11}$.

When Z is an optionally substituted C$_{2-10}$ alkenyl, or an optionally substituted C$_{2-10}$ alkynyl these moieties may also, in addition to those substituent groups noted above, also be optionally substituted with aryl, aryl C$_{1-4}$ alkyl, heteroaryl, and heteroaryl C$_{1-4}$ alkyl groups (which aryl and heteroaryl containing moieties may be optionally substituted).

In compounds of Formula (I), when Z is a heteroaryl (HET) ring, it is suitably a heteroaryl ring or ring system. If the HET moiety is a multi ring system, the ring containing the heteroatom does not need to be directly attached to the urea moiety. All the rings in this ring system may be optionally substituted as defined herein. Preferably the HET moiety is a pyridyl, which may be 2-, 3- or 4-pyridyl. If the ring is a multi system ring it is preferably benzimidazole, dibenzothiophene, or an indole ring. Other heterocyclic rings of interest include, but are not limited to thiophene, furan, pyrimidine, pyrrole, pyrazole, quinoline, isoquinoline, quinazolinyl, pyridine, oxazole, thiazole, thiadiazole, triazole, imidazole, or benzimidazole.

In compounds of Formula (I), the HET ring may be optionally substituted independently by the (Y)$_n$ term as defined above.

As used herein, "optionally substituted" unless specifically defined shall mean such groups as halogen, such as fluorine, chlorine, bromine or iodine; hydroxy; hydroxy substituted C$_{1-10}$alkyl; C$_{1-10}$ alkoxy, such as methoxy or ethoxy; S(O)$_{m'}$ C$_{1-10}$ alkyl, wherein m' is 0, 1 or 2, such as methyl thio, methyl sulfinyl or methyl sulfonyl; amino, mono & di-substituted amino, such as in the NR$_4$R$_5$ group; NHC(O)R$_4$; C(O)NR$_4$R$_5$; C(O)OH; S(O)$_2$NR$_4$R$_5$; NHS(O)$_2$R$_{19}$, C$_{1-10}$ alkyl, such as methyl, ethyl, propyl, isopropyl, or t-butyl; halosubstituted C$_{1-10}$ alkyl, such CF$_3$; an optionally substituted aryl, such as phenyl, or an optionally substituted arylalkyl, such as benzyl or phenethyl, optionally substituted heterocylic, optionally substituted heterocylicalkyl, optionally substituted heteroaryl, optionally substituted heteroaryl alkyl, wherein these aryl, heteroaryl, or heterocyclic moieties may be substituted one to two times by halogen; hydroxy; hydroxy substituted alkyl; C$_{1-10}$ alkoxy; S(O)$_{m'}$C$_{1-10}$ alkyl; amino, mono & di-substituted amino, such as in the NR$_4$R$_5$ group; C$_{1-10}$ alkyl, or halosubstituted C$_{1-10}$ alkyl, such as CF$_3$.

R$_{19}$ is suitably C$_{1-4}$ alkyl, aryl, aryl C$_{1-4}$alkyl, heteroaryl, heteroarylC$_{1-4}$alkyl, heterocyclic, or heterocyclicC$_{1-4}$alkyl.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo.

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic radicals, preferably of 3 to 8 carbons, including but not limited to cyclopropyl, cyclopentyl, cyclohexyl, and the like.

"alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, benzimidazole, or benzthiazole.

"heterocyclic" (on its own or in any combination, such as "heterocyclicalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

"arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

"sulfinyl"—the oxide S(O) of the corresponding sulfide, the term "thio" refers to the sulfide, and the term "sulfonyl"0 refers to the fully oxidized $S(O)_2$ moiety.

The term "wherein two $R_1$ moieties (or two Y moieties) may together form a 5 or 6 membered saturated or unsaturated ring" is used herein to mean the formation of a ring system, such as a naphthalene ring system or a phenyl moiety having attached a 6 membered partially unsaturated ring attached, such as a $C_6$ cycloalkenyl, i.e. hexene, or a $C_5$ cycloalkenyl moiety, cyclopentene.

Exemplified compounds of Formula (I) include:

N-[(1,3)-Dihydro-2,2-dioxo-3-methyl-4-chloro-2,1-benzisothiazo)-7-yl]-N'-[2-bromophenyl]urea N-[(1,3)-Dihydro-2,2-dioxo-3-propyl-4-chloro-2,1-benzisothiazo)-7-yl]-N'-[2-bromophenyl]urea N-[(1-hydro-2,2-dioxo-3,3-dimethyl-4-chloro-2,1-benzisothiazo)-7-yl]-N'-[2-bromophenyl]urea N-[(1,3)-Dihydro-2,2-dioxo-3-fluoro-4-chloro-2,1-benzisothiazo)-7-yl]-N'-[2-bromophenyl]urea N-[(1,3)-Dihydro-2,2-dioxo-3-methylamide-4-chloro-2,1-benzisothiazo)-7-yl]-N'-[2-bromophenyl]urea N-[(1,3)-Dihydro-2,2-dioxo-3-methyl-3-methylamide-4-chloro-2,1-benzisothiazo)-7-yl]-N'-[2-bromophenyl]urea N-[(1,3)-Dihydro-2,2-dioxo-3-methylene-4-chloro-2,1-benzisothiazo)-7-yl]-N'-[2-bromophenyl]urea N-[(1,3)-Dihydro-2,2-dioxo-3-(benzisothiazo-2-yl)-4-chloro-2,1-benzisothiazo)-7-yl]-N'-[2-bromophenyl]urea It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

Methods of Preparation

The compounds of Formula (I) may be obtained by applying synthetic procedures, some of which are illustrated in the Schemes below. The synthesis provided for in these Schemes is applicable for the producing of Formula (I) having a variety of different Z, $R_1$, and E' groups which are reacted, employing optional substituents which are suitably protected to achieve compatibility with the reactions outlined herein. Subsequent deprotection, in those cases, then affords compounds of the nature generally disclosed. Once the urea nucleus has been established, further compounds of these formulas may be prepared by applying standard techniques for functional group interconversion, well known in the art. While the schemes are shown with various compounds of Formula (I) this is merely for illustration purposes only and not a limitation on the extent of synthesis available using these methods.

Scheme 1

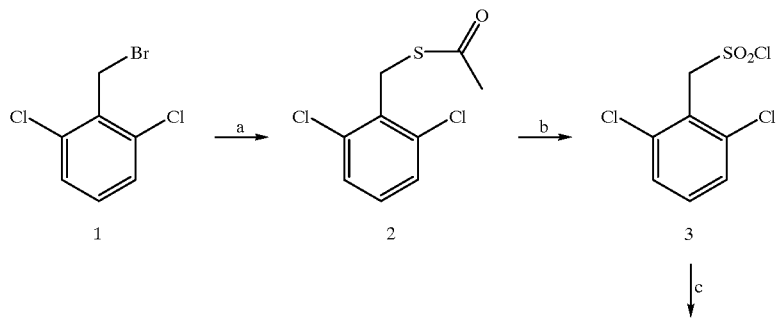

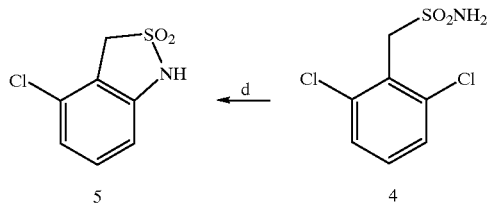

a) KSC(=O)CH₃ b) Cl₂, AcOH/H₂O
c) NH₄OH d) K₂CO₃, Cu

If the desired heterocyclic compound 5-scheme 1 is not commercially available, the commercially available 2,6-dichlorobenzylbromide can be treated with potassium thioacetate to form the thioacetate 2-scheme 1, followed by oxidation using chlorine gas in AcOH/H₂O or sulfuryl chloride and acetic anhydride to form the sulfonyl chloride 3-scheme 1. The sulfonyl chloride can be converted to the corresponding sulfonamide 4-scheme 1 by using NH₄OH followed by acidification or using ammonia gas in a suitable organic solvent such as methylene chloride. The cyclic sulfonamide 5-scheme 1 can be cyclized under basic condition such as potassium carbonate, and copper metal, as a catalyst followed by acidification.

dium catalyst in the presence of a reducing agent such as sodium borohydride, tributyl tin hydride or an organic acid such as 2-ethylhexanoic acid. The nitro compound 5-scheme 2 can be prepared from 4-scheme 2, using standard nitration conditions such as sodium nitrate in sulfuric acid and water, ammonium nitrate and trifluoroacetic acid, or nitric acid in acetic anhydride.

The unsaturated cyclic sulfonamide 3-scheme 3 can be prepared from the sulfonamide 2-scheme 3 by alkylation with the desired 2-substituted alkyl halide and a base such as hexamethyldisilazane in the appropriate organic solvent such as THF followed by contaminant elimination. The nitro compound 4-scheme 3 can be prepared from the sulfona- Scheme 2

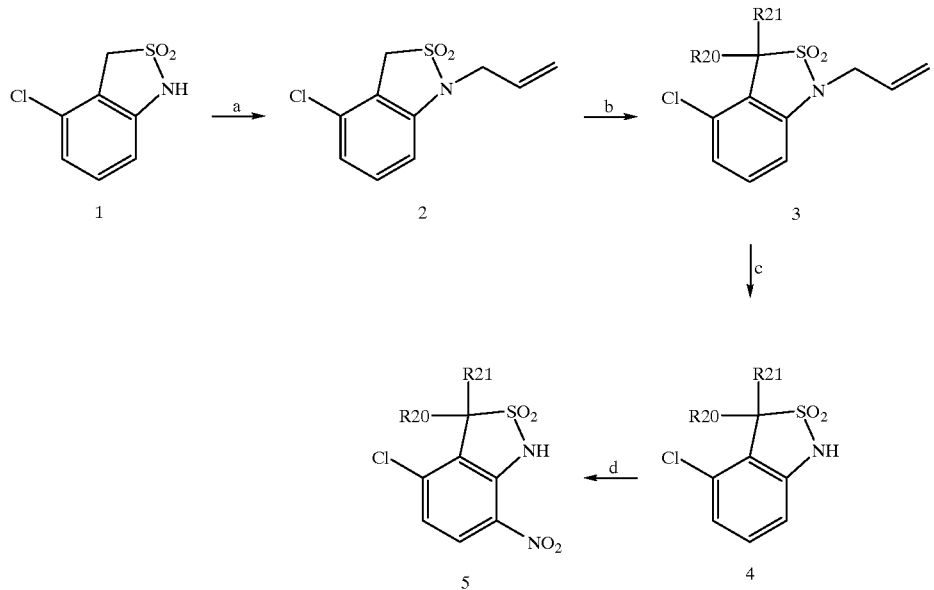

R₂₀ = H, H    R₂₁ = Me, propyl
a) NaH, allyl bromide b) Na[(CH₃)₃Si]₂N, MeI or CH₃(CH₂)₂I
c) NaBH₄, Pd(Ph₃)₄ d) NaNO₃, H₂SO₄/H₂O or NH₄NO₃, TFAA Cyclic sulfonamide 4-scheme 2 can be prepared by protection of the nitrogen compound 1-scheme 2 preferably as the allyl compound using allyl bromide and a base such as sodium hydride. Alkylation of 2-scheme 2 with the desired alkyl halide in the presence of a suitable base such as sodium hexamethyldisilazane gives compound 3-scheme 2. Compound 4-scheme 2 can be obtained by removal of the allyl group under suitable conditions, preferably using a pallamide 3-scheme 3 by first removal of the allyl group by standard conditions such as a palladium catalyst in the presence of a reducing agent such as sodium borohydride, tributyltin hydride or an organic acid such as 2-ethylhexanoic acid, and second incorporation of the nitro functionality by standard nitrating conditions such as sodium nitrate in sulfuric acid and water, ammonium nitrate and trifluoroacetic acid, or nitric acid in acetic anhydride.

Scheme 3

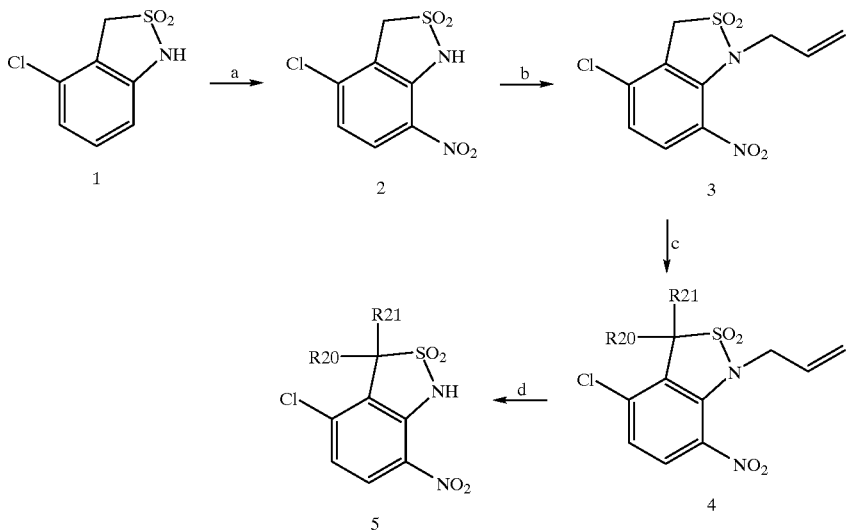

$R_{20}$ = Me, H    $R_{21}$ = Me, F
a) NaNO$_3$, H$_2$SO$_4$/H$_2$O  b) NaH, allyl bromide
c) NaH, MeI or Li[(CH$_3$)$_3$Si]N, (PhSO$_2$)$_2$NF  d) NaBH$_4$, Pd(Ph$_3$)$_4$ An alternative method for forming the nitro compound 5-scheme-2 is shown in Scheme 3. The nitro compound 2-Scheme 3 can be prepared from 1-scheme 3, under standard nitration conditions such as sodium nitrate in sulfuric acid and water, ammonium nitrate and trifluoroacetic acid, or nitric acid in acetic anhydride. The compound, 5-Scheme 3 can be obtained using the same series of reactions, and conditions outlined above for compound 5-scheme 2.

Scheme 4

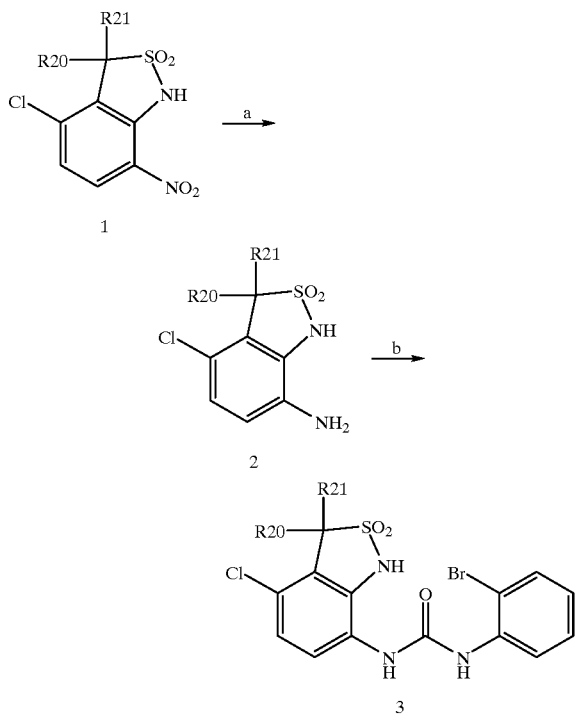

-continued
a) SnCl$_2$, EtOH  b) 2-BrPhNCO, DMF

The compound 3-scheme 4 can be obtained form the nitro compound 1-scheme 4 using standard reduction conditions preferably SnCl$_2$ in EtOH to give the aniline 2-scheme 4. Ortho substituted heterocyclic phenyl ureas in 3-scheme 4 may be prepared under standard conditions, such as by condensation of the desired aryl isocyanate (commercially available) with the corresponding aniline 2-scheme 4 in an aprotic solvent such as DMF at room temperature or heating.

Another aspect of the present invention is an analogous process for producing compounds of Formula (I), which process comprises reacting a compound of the formula:

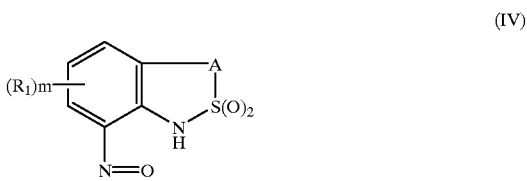

(IV)

wherein A, $R_1$, and m are as defined for Formula (I);
with a compound of the formula:

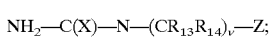

NH$_2$—C(X)—N—(CR$_{13}$R$_{14}$)$_v$—Z;

wherein X, $R_{13}$, $R_{14}$, v and Z are as defined in Formula (I) to yield a compound of Formula (I) and thereafter if necessary, deprotecting, or converting a precursor of $R_1$, A, or Z to a group $R_1$, A or Z.

In this process the desired isocyanate, a compound of Formula (IV) is made by condensing the amine of 2-Scheme 4 with triphosgene in the presence of base (such as potassium carbonate) or by reacting the carboxylic acid with diphenyl phosphoazide in the presence of a base (such as triethyl amine).

An alternative process for making compounds of Formula (I) is a process which comprises a) reacting a compound of the formula:

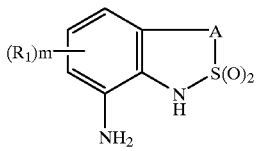
(II)

wherein A, $R_1$, and m are as defined in Formula (I); with a compound of the formula:

$C(X)-N-(CR_{13}R_{14})_v-Z$;

wherein A, $R_1$, m, X, $R_{13}$, $R_{14}$, v and Z are as defined in Formula (I) to yield a compound of Formula (I), and thereafter if necessary, deprotecting, or converting a precursor of $R_1$, A, or Z to a group $R_1$, A or Z.

Another aspect of the present invention is a process for making a compound of the formula:

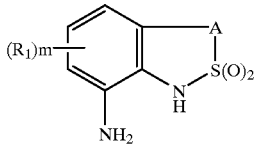
(II)

wherein $R_1$, m and A are as defined for Formula (I); by reducing a compound of the formula:

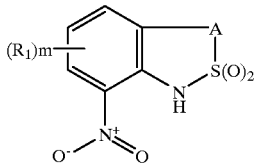
(IV)

wherein $R_1$, m and A are as defined for Formula (I); under suitable conditions to yield a compound of Formula (II).

Another aspect of the present invention are the novel compounds of Formula (III) as represented by the structure:

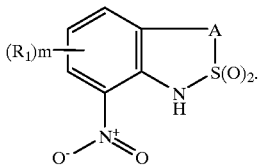
(III)

wherein $R_1$, m and A are as defined for Formula (I).

Another aspect of the present invention are the novel compounds of Formula (II) as represented by the structure:

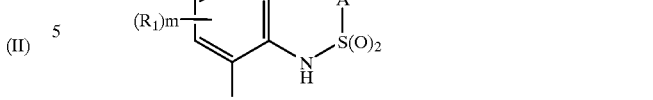
(II)

wherein $R_1$, m and A are as defined for Formula, (I).

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Example 1

Preparation of N-[(1,3)-Dihydro-2,2-dioxo-3-methyl-4-chloro-2,1-benzisothiazo)-7-yl]-N'-[2-bromophenyl]urea a) Preparation of 2,6-Dichlorobenzylthioacetate To a solution of 2,6-dichlorobenzylbromide (30 grams (hereinafter "g"), 125.5 millimoles (hereinafter "mmol")) in DMF (30 millliliters (hereinafter "ml")), potassium thioacetate (15.65 g, 138 mmol) was added. The reaction mixture was stirred at room temperature for about one hour. Then it was partitioned between ethyl acetate and water. The combined organic phase was dried and concentrated to give the desired product (29.3 g, 99%). EI-MS m/z 241 (M$^+$).

b) Preparation of 2,6-dichlorobenzylsulfonylchloride

The 2,6-dichlorobenzylthioacetate (29 g, 121 mmol) and sodium acetate (68 g) were dissolved in a mixture of glacial acetic acid (646 ml) and water (141 ml). Chlorine gas was passed into the solution for about 10 min. The mixture was evaporated and the residue was extracted with ethyl acetate. The combined organic phase was dried and concentrated to give the desired product (27 g, 86%). EI-MS m/z 260.5 (M$^+$).

c) Preparation of 2,6-dichlorobenzylsulfonamide

The 2,6-dichlorobenzylsulfonylchloride (27 g, 103.6 mmol) in ammonium hydroxide (270 ml) was stirred at room temperature for about 3 hours. On acidification with cooled concentrated hydrochloric acid a precipitate separated and was filtered to give desired product (16 g, 64%) EI-MS m/z 239 (M$^-$).

d) Preparation of 1,3-dihydro-2,2-dioxo-4-chloro-2,1-benzisothiazole

The 2,6-dichlorobenzylsulfonamide (8 g, 33.47 mmol) was added to potassium carbonate (4.62 g, 33.47 mmol), copper powder (560 milligram (hereinafter "mg")) and N,N-dimethylaniline (10 ml) in a round bottom flask. The reaction mixture was stirred at 170° C. for about 4 hours. then was cooled to room temperature and partitioned between ethyl acetate and 10% aqueous HCl. The combined organic phase was dried and concentrated. Chromatography of the residue on silica gel (30% Ethyl acetate/Hexane) gave desired product (4 g, 59%). EI-MS m/z 204.5 (M$^+$).

e) Preparation of 1-allyl-3-hydro-2,2-dioxo-4-chloro-2,1-benzisothiazole

To a solution of 1,3-dihydro-2,2-dioxo-4-chloro-2,1-benzisothiazole (3.18 g, 15.63 mmol) in DMF (15 ml), sodium hydride (60%, 625 mg, 15.63 mmol) and allyl bromide (1.6 ml, 17.2 mmol) were added. The reaction mixture was stirred at room temperature for about 16 hours. Then it was partitioned between ethyl acetate and 10% aqueous HCl. The combined organic phase was dried and concentrated. Chromatography of the residue on silica gel (20% Ethyl acetate/Hexane) gave desired product (3 g, 79%). EI-MS m/z 244.5 (M$^+$).

f) Preparation of 1-allyl-3-hydro-2,2-dioxo-3-methyl-4-chloro-2,1-benzisothiazole To a solution of 1 -allyl-3-hydro-2,2-dioxo-4-chloro-2,1-benzisothiazole (456 mg, 1.87 mmol) in THF (10 ml) at −78° C., sodium bis(trimethylsilyl)amide (1.0 M in THF, 1.87 ml, 1.87 mmol) was added. The reaction mixture was stirred at room temperature for about 30 min. Then was cooled down to −78° C. again, methyl iodide (0.14 ml, 2.25 mmol) was added. The reaction mixture was stirred at room temperature for 1 hour. Then was partitioned between ethyl acetate and 10% of HCl. The combined organic phase was dried and concentrated. Chromatography of the residue on silica gel (10% Ethyl acetate/Hexane) gave desired product (330 g, 68%). EI-MS m/z 258.5 (M$^+$).

g) Preparation of 1,3-dihydro-2,2-dioxo-4-chloro-3-methyl-2,1-benzisothiazole

To a solution of 1-allyl-3-hydro-2,2-dioxo-4-chloro-3-methyl-2,1-benzisothiazole (330 mg, 1.27 mmol) in THF (10 ml), sodium borohydride (104.6 mg, 2.54 mmol) and tetrakis(triphenylphosphine)palladium(0) (59 mg, 0.05 mmol) were added. The reaction mixture was stirred at room temperature for about 16 hours. Then was partitioned between ethyl acetate and 10% aqueous HCl. The combined organic phase was dried and concentrated. Chromatography of the residue on silica gel (50% Ethyl acetate/Hexane) gave desired product (200 g, 72%). EI-MS m/z 218.5 (M$^+$).

h) Preparation of 1,3-dihydro-2,2-dioxo4-chloro-7-nitro-3-methyl-2,1-benzisothiazole 1,3-dihydro-2,2-dioxo-4-chloro-3-methyl-2,1-benzisothiazole (200 mg, 0.92 mmol) was dissolved in methylene chloride (30 ml) followed by the addition of sodium nitrate (86 mg, 1.01 mmol). The addition of sulfuric acid (0.18 ml/3M) is then made, followed by addition of a catalytic amount of sodium nitrite. The mixture is allowed to stir. After about 24 hours, the reaction mixture is diluted with methylene chloride and extracted with water. The organic layer is dried over MgSO$_4$ and filtered. The solvent was evaporated and chromatography of the resulting solid on silica gel (50% Ethyl acetate/Hexane) gave the desired product (50 mg, 21%). EI-MS m/z 263.5 (M$^+$).

i) Preparation of 1,3-dihydro-2,2-dioxo-4-chloro-3-methyl-7-amino-2,1-benzisothiazole To the solution of 1,3-dihydro-2,2-dioxo-4-chloro-3-methyl-7-nitro-2,1-benzisothiazole (50 mg, 0.19 mmol) in ethanol (5 ml), Tin (II) chloride (214 mg, 0.95 mmol) was added. The reaction mixture was stirred at reflux for about 4 hours. Then was cooled to room temperature. NaHCO$_3$ (aqueous) was added to the reaction mixture until pH=7. Then the solution was extracted with ethyl acetate (3×). The combined organic layer was dried over MgSO$_4$, filtered and concentrated under reduced pressure to give desired product (32 mg, 72%). EI-MS m/z 233.5 (M$^+$)

j) Preparation of N-[(1,3)-Dihydro-2,2-dioxo-3-methyl-4-chloro-2,1-benzisothiazo)-7-yl]-N'-[2-bromophenyl]urea To a solution of 2-bromo phenyl isocyanate (26 mg, 0.13 mmol) in DMF (1.0 ml), 1,3-dihydro-2,2-dioxo-4-chloro-7-amino-2,1-benzisothiazole (32 mg, 0.13 mmol) was added. The reaction mixture was stirred at room temperature for about 16 hours. Chromatography of the resulting liquid on silica gel (50% Ethyl acetate/Hexane) gave desired product (30 mg, 50%). EI-MS m/z 430 (+).

Example 2

Preparation of N-[(1,3)-Dihydro-2,2-dioxo-3-propyl-4-chloro-2,1-benzisothiazo)-7t-yl]-N'-[2-bromophenyl]urea a) Preparation of 1-allyl-3-hydro-2,2-dioxo-3-propyl-4-chloro-2,1-benzisothiazole Following the procedure of Example (1f) except substituting propyl iodide for methyl iodide, the title compound was prepared in 43% yield. EI-MS m/z 286.5 (M$^+$).

b) Preparation of, 3-dihydro-2,2-dioxo-4-chloro-3-propyl-2,1-benzisothiazole

Following the procedure of Example (1g), the title compound was prepared in 76% yield. EI-MS m/z 244.1 (M$^+$).

c) Preparation of 1,3-dihydro-2,2-dioxo4-chloro-3-propyl-7-nitro-2,1-benzisothiazole 1,3-dihydro-2,2-dioxo-4-chloro-3-propyl-2,1-benzisothiazole (131 mg, 0.54 mmol) was dissolved in chloroform (30 ml) followed by the addition of ammonium nitrate (44 mg, 0.54 mmol) and trifluoroacetic anhydride (397 mg, 214.4 mmol). The mixture is allowed to stir. After 24 hours, the reaction mixture is diluted with chloroform and extracted with water. The organic layer is dried over MgSO$_4$ and filtered. The solvent was evaporated and chromatography of the resulting solid on silica gel (50% Ethyl acetate/Hexane) gave the desired product (28 mg, 20%). EI-MS m/z 289.1 (M$^+$).

d) Preparation of 1,3-dihydro-2,2-dioxo-4-chloro-3-propyl-7-amino-2,1-benzisothiazole Following the procedure of Example (1i), the title compound was prepared in 92% yield. EI-MS m/z 261.1 (M$^+$).

e) Preparation of N-[(1,3)-Dihydro-2,2-dioxo-3-propyl-4-chloro-2,1-benzisothiazo)-7-yl]-N'-[2-bromophenyl]urea Following the procedure of Example (1j), the title compound was prepared in 49% yield. EI-MS m/z 456,1, 458.2 (M$^-$).

Example 3

Preparation of N-[(1-hydro-2,2-dioxo-3,3-dimethyl-4-chloro-2,1-benzisothiazo)-7-yl]-N'-[2-bromophenyl]urea a) Preparation of 1,3-dihydro-2,2-dioxo-4-chloro-7-nitro-2,1-benzisothiazole 1,3-dihydro-2,2-dioxo-4-chloro-2,1-benzisothiazole (1.5 mg, 0.92 mmol) was dissolved in methylene chloride (30 ml) followed by the addition of sodium nitrate (86 mg, 1.01 mmol). The addition of sulfuric acid (0.18 ml/3M) is then made, followed by addition of a catalytic amount of sodium nitrite. The mixture is allowed to stir. After about 24 hours, the reaction mixture is diluted with methylene chloride and extracted with water. The organic layer is dried over $MgSO_4$ and filtered. The solvent was evaporated and chromatography of the resulting solid on silica gel (50% Ethyl acetate/Hexane) gave the desired product(50 mg, 21%). EI-MS m/z 263.5 ($M^+$).

b) Preparation of 1-allyl-2,2-dioxo-3,3-dihydro-4-chloro-7-nitro-2,1-benzisothiazole To a solution of 1,3-dihydro-2,2-dioxo-4-chloro-2,1-benzisothiazole (1.1 g, 4.43 mmol) in DMF (20 ml), Sodium hydride (60%, 178 mg, 4.43 mmol) and allyl bromide (0.42 ml, 4.87 mmol) were added. The reaction mixture was stirred at 60° C. for about 3 hours then cooled to room temperature for about 16 hours. The reaction mixture was partitioned between ethyl acetate and 10% of HCl. The combined organic phase was dried and concentrated. Chromatography of the residue on silica gel (20% Ethyl acetate/Hexane) gave desired product (800 mg, 65%). EI-MS m/z 289.1 ($M^+$).

c) Preparation of 1-allyl-2,2-dioxo-3,3-dimethyl-4-chloro-7-nitro-2,1-benzisothiazole To a solution of 1-allyl-2,2-dioxo-3,3-dihydro-4-chloro-7-nitro-2,1-benzisothiazole (100 mg, 0.35 mmol) in DMF (5 ml), sodium hydride (60%, 28 mg, 0.7 mmol) was added. After stirring at room temperature for about 30 min., iodomethane (99.4 mg, 0.7 mmol) was added. Then the reaction mixture was stirred at 70°C. for 2 hours. The reaction mixture was partitioned between ethyl acetate and 10% of HCl. The combined organic phase was dried and concentrated. Chromatography of the residue on silica gel (10% Ethyl acetate/Hexane) gave desired product (87 mg, 80%). EI-MS m/z 317.2 ($M^+$).

d) Preparation of 1-hydro-2,2-dioxo-3,3 -dimethyl-4-chloro-7-nitro-2,1-benzisothiazole Following the procedure of Example (1g), the title compound was prepared in 45% yield. EI-MS m/z 277.2 ($M^-$).

e) Preparation of 1-hydro-2,2-dioxo-3,3-dimethyl-4-chloro-7-amino-2,1-benzisothiazole Following the procedure of Example (1i), the title compound was prepared in 98% yield. EI-MS m/z 247.1 ($M^-$).

f) Preparation of N-[(1-hydro-2,2-dioxo-3,3-dimethyl-4-chloro-2,1-benzisothiazo)-7-yl]-N'-[2-bromophenyl]urea Following the procedure of Example (1j), the title compound was prepared in 52% yield. EI-MS m/z 443.1, 445.2 ($M^-$).

Example 4

Preparation of N-[(1,3)-Dihydro-2,2-dioxo-3-fluoro-4-chloro-2,1-benzisothiazo)-7-yl]-N'-[2-bromophenyl]urea a) Preparation of 1-allyl-3,3-dihydro-2,2-dioxo-4-chloro-7-nitro-2,1-benzisothiazole To a solution of 1-allyl-2,2-dioxo-3,3-dihydro-4-chloro-7-nitro-2,1-benzisothiazole (358 mg, 1.24 mmol) in THF (15 ml) at −78° C., lithium bis(trimethylsilyl)amide (1.0M in THF, 1.49 ml, 1.49 mmol) was added. The reaction mixture was stirred at −78° C. for about 1 hour, then N-fluorobenzenesulfonimide (547 mg, 2.25 mmol) was added. The reaction mixture was stirred at room temperature for about 1 hour. Then was partitioned between ethyl acetate and 10% of HCl. The combined organic phase was dried and concentrated. Chromatography of the residue on silica gel (10% Ethyl acetate/Hexane) gave desired product (200 mg, 53%). EI-MS m/z 307.1 ($M^+$).

b) Following the procedure of Example (1g) except substituting 1-hydro-2,2-dioxo-3-hydro-3-floro-4-chloro-7-nitro-2,1-benzisothiazole for 1,3-dihydro-2,2-dioxo-3-methyl-4-chloro-2,1-benzisothiazole, the title compound was prepared in 62% yield. EI-MS m/z 267.1 ($M^+$).

c) Preparation of 1,3-dihydro-2,2-dioxo-3-fluoro-4-chloro-3-methyl-7-amino-2,1-benzisothiazole To the solution of 1,3-dihydro-2,2-dioxo-4-chloro-3-fluoro-7-nitro-2,1-benzisothiazole (100 mg, 0.4 mmol) in ethanol (10 ml), Tin (II) chloride (443 mg, 2.0 mmol) was added. The reaction mixture was stirred at room temperature for about 16 hours. Then all solvent was evaporated. Chromatography of the residue on silica gel (50% Ethyl acetate/Hexane) gave desired product (43 mg, 47%). EI-MS m/z 237.2 ($M^+$).

d) Preparation of N-[(1,3)-Dihydro-2,2-dioxo-3-fluoro-4-chloro-2,1-benzisothiazo)-7-yl]-N'-[2-bromophenyl]urea To a solution of 2-bromo phenyl isocyanate (25 mg, 0.13 mmol) in DMF (1.0 ml), 1,3-dihydro-2,2-dioxo-3-fluoro-4-chloro-7-amino-2,1-benzisothiazole (30 mg, 0.13 mmol) was added. The reaction mixture was stirred at room temperature for about 16 hours. The product was purified by precipitation from methylene chloride and hexane and filtering (17 mg, 31%). EI-MS m/z 434.1, 436.1 ($M^-$).

Using analogous methods to those indicated above the following compounds have been prepared:

Example 5

N-[(1,3)-Dihydro-2,2-dioxo-3-methylamide-4-chloro-2,1-benzisothiazo)-7-yl]-N'-[2-bromophenyl]urea MS(EI) m/e 473.2 (m−$H^{31}$ )

Example 6

N-[(1,3)-Dihydro-2,2-dioxo-3-methyl-3-methylamide-4-chloro-2,1-benzisothiazo)-7-yl]-N'-[2-bromophenyl]urea MS(EI) m/e 473.2 (m−$H^-$)

Example 7

N-[(1,3)-Dihydro-2,2-dioxo-3-methylene-4-chloro-2,1-benzisothiazo)-7-yl]-N'-[2-bromophenyl]urea MS(EI) m/e 472.2 (m−$H^-$)

Example 8

N-[(1,3)-Dihydro-2,2-dioxo-3-(benzothiazol-2-yl)-4-chloro-2,1-benzisothiazo)-7-yl]-N'-[2-bromophenyl]urea m.p. 145–152° C.

Method of Treatment

The compounds of Formula (I), or a pharmaceutically acceptable salt thereof can be used in the manufacture of a medicament for the prophylactic or therapeutic treatment of any disease state in a human, or other mammal, which is exacerbated or caused by excessive or unregulated IL-8 cytokine production by such mammal's cell, such as but not limited to monocytes and/or macrophages, or other chemokines which bind to the IL-8 α or β receptor, also referred to as the type I or type II receptor.

Accordingly, the present invention provides a method of treating a chemokine mediated disease, wherein the chemokine is one which binds to an IL-8 α or β receptor and which method comprises administering an effective amount of a compound of Formula (I) or a pharmaceutically acceptable salt thereof. In particular, the chemokines are IL-8, GROα, GROβ, GROγ, NAP-2 or ENA-78.

The compounds of Formula (I) are administered in an amount sufficient to inhibit cytokine function, in particular IL-8, GROα, GROβ, GROγ, NAP-2 or ENA-78, such that they are biologically regulated down to normal levels of physiological function, or in some case to subnormal levels, so as to ameliorate the disease state. Abnormal levels of IL-8, GROα, GROβ, GROγ, NAP-2 or ENA-78 for instance in the context of the present invention, constitute: (i) levels of free IL-8 greater than or equal to 1 picogram per mL; (ii) any cell associated IL-8, GROα, GROβ, GROγ, NAP-2 or ENA-78 above normal physiological levels; or (iii) the presence IL-8, GROα, GROβ, GROγ, NAP-2 or ENA-78 above basal levels in cells or tissues in which IL-8, GROα, GROβ, GROγ, NAP-2 or ENA-78 respectively, is produced.

There are many disease states in which excessive or unregulated IL-8 production is implicated in exacerbating and/or causing the disease. Chemokine mediated diseases include psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, Alzheimer's disease, allograft rejections, malaria, restinosis, angiogenesis or undesired hematopoietic stem cells release, rhinovirus infections, and various bone resorptive indications, such as osteoporosis or osteoarthritis.

The association of interleukin-8 and rhinovirus may be found in articles such as: Turner, et al., Clin. Infect. Dis. (1998), 26(4), 840–846; Sanders, et al., J. Virol. (1998), 72(2), 934–942; Sethi, et al., Clin. Exp. Immunol. (1997), 110(3), 362–369; Zhu, et al., Am. J. Physiol. (1997), 273(4, Pt. 1), L814–L824; Terajima, et al., Am. J. Physiol. (1997), 273(4, Pt. 1), L749–L759; Grunberg, et al., Clin. Exp. Allergy (1997), 27(1), 36–45; and Johnston, et al., J. Infect. Dis. (1997), 175(2), 323–329.

The association of interleukin-8 and osteoporosis may be found in articles such as: Streckfus et al., J. Gerontol., Ser. A (1997), 52A(6), M343–M351; Hermann, T. WO 95/31722; and Chaudhary, et al., Endocrinology (Baltimore) (1992), 130(5), 2528–34.

These diseases are primarily characterized by massive neutrophil infiltration, T-cell infiltration, or neovascular growth, and are associated with IL-8, GROα, GROβ, GROγ, NAP-2 or ENA-78 production which is responsible for the chemotaxis of neutrophils into the inflammatory site or the directional growth of endothelial cells. In contrast to other inflammatory cytokines (IL-8, GROα, GROβ, GROγ, or NAP-2) has the unique property of promoting neutrophil chemotaxis, enzyme release including but not limited to elastase release as well as superoxide production and activation. The α-chemokines but particularly, GROα, GROβ, GROγ, or NAP-2, working through the IL-8 type I or II receptor can promote the neovascularization of tumors by promoting the directional growth of endothelial cells. Therefore, the inhibition of IL-8 induced chemotaxis or activation would lead to a direct reduction in the neutrophil infiltration.

Recent evidence also implicates the role of chemokines in the treatment of HIV infections, Littleman et al., Nature 381, pp. 661 (1996) and Koup et al., Nature 381, pp. 667 (1996).

The present invention also provides for a means of treating, in an acute setting, as well as preventing, in those individuals deemed susceptible to, CNS injuries by the chemokine receptor antagonist compounds of Formula (I).

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this are has been emerging and the present invention provides a mean for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. See Liu et al., Stoke, Vol. 25., No. 7, pp. 1481–88 (1994) whose disclosure is incorporated herein by reference.

Models of closed head injuries and treatment with mixed 5-LO/CO agents is discussed in Shohami et al., J. of Vaisc & Clinical Physiology and Pharmacology, Vol. 3, No. 2, pp. 99–107 (1992) whose disclosure is incorporated herein by reference. Treatment which reduced edema formation was found to improve functional outcome in those animals treated.

Present evidence also indicates the use of IL-8 inhibitors in the treatment of atherosclerosis. The first reference, Boisvert et al., J. Clin. Invest., 1998, 101:353–363 shows, through bone marrow transplantation, that the absence of IL-8 receptors on stem cells (and, therefore, on monocytes/macrophages) leads to a reduction in the development of atherosclerotic plaques in LDL receptor deficient mice. Additional supporting references are: Apostolopoulos, et al., Arterioscler Thromb Vasc Biol. 1996, 16:1007–1012; Liu, et al., Arterioscler Thromb Vasc Biol, 1997, 17:317–323; Rus, et al., Atherosclerosis. 1996, 127:263–271.: Wang et al., J Biol Chem. 1996, 271:8837–8842; Yue, et al., Eur J Pharmacol. 1993, 240:81–84; Koch, et al., Am J Pathol, 1993, 142:1423–1431.; Lee, et al., Immunol Lett, 1996,53, 109–113.; and Terkeltaub et al., Arterioscler Thromb, 1994, 14:47–53.

The compounds of Formula (I) are administered in an amount sufficient to inhibit IL-8, binding to the IL-8 alpha or beta receptors, from binding to these receptors, such as evidenced by a reduction in neutrophil chemotaxis and activation. The discovery that the compounds of Formula (I) are inhibitors of IL-8 binding is based upon the effects of the compounds of Formulas (I) in the in vitro receptor binding assays which are described herein. The compounds of Formula (I) have been shown to be inhibitors of type II IL-8 receptors.

As used herein, the term "IL-8 mediated disease or disease state" refers to any and all disease states in which IL-8, GROα, GROβ, GROγy, NAP-2 or ENA-78 plays a role, either by production of IL-8, GROα, GROβ, GROγ, NAP-2 or ENA-78 themselves, or by IL-8, GROα, GROβ, GROγ, NAP-2 or ENA-78 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "chemokine mediated disease or disease state" refers to any and all disease states in which a chemokine which binds to an IL-8 α or β receptor plays a role, such as but not limited IL-8, GROα, GROβ, GROγ, NAP-2 or ENA-78. This would include a disease state in which, IL-8 plays a role, either by production of IL-8 itself, or by IL-8 causing another monokine to be released, such as but not limited to IL-1, IL-6 or TNF. A disease state in which, for instance, IL-1is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1(IL-1), Interleukin-6 (IL-6), Interleukin-8 (IL-8), Tumor Necrosis Factor-alpha (TNF-α and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells. B-cells, endothelial cells and smooth muscle cells. Examples of chemokines include, but are not limited to, IL-8, GRO-α, GRO-β, GRO-γ, NAP-2, ENA-78, IP-10, MIP-α, MIP-β, PF4, and MCP 1, 2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0. 1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or nonaqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01 %) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

Biological Examples

The IL-8, and GRO-α chemokine inhibitory effects of compounds of the present invention are determined by the following in vitro assay:

Receptor Binding Assays

[$^{125}$I] IL-8 (human recombinant) is obtained from Amersham Corp., Arlington Heights, Ill., with specific activity 2000 Ci/mmol. Gro-α is obtained from NEN—New England Nuclear. All other chemicals are of analytical grade. High levels of recombinant human IL-8 type α and β receptors were individually expressed in Chinese hamster ovary cells as described previously (Holmes, et al., *Science*, 1991, 253, 1278). The Chinese hamster ovary membranes were homogenized according to a previously described protocol (Haour, et al., *J Biol Chem.*, 249 pp. 2195–2205 (1974)). Except that the homogenization buffer is changed to 10 mM Tris-HCl, 1mM MgSO4, 0.5mM EDTA (ethylenediaminetetra-acetic acid), 1 mMPMSF (α-toluenesulphonyl fluoride), 0.5 mg/L Leupeptin, pH 7.5. Membrane protein concentration is determined using Pierce Co. micro-assay kit using bovine serum albumin as a standard. All assays are performed in a 96-well micro plate format. Each reaction mixture contains $^{125}$I IL-8 (0.25 nM) or $^{125}$I Gro-α and 0.5 μg/mL of IL-8Rα or 1.0 μg/mL of IL-8Rβ membranes in 20 mM Bis-Trispropane and 0.4 mM Tris HCl buffers, pH 8.0, containing 1.2 mM MgSO$_4$, 0.1 mM EDTA, 25 mM NaCl and 0.03% CHAPS. In addition, drug or compound of interest is added which has been pre-dissolved in DMSO so as to reach a final concentration of between 0.01 nM and 100 uM. The assay is initiated by addition of $^{125}$I-IL-8. After 1 hour at room temperature the plate is harvested using a Tomtec 96-well harvester onto a glass fiber filtermat blocked with 1% polyethylenimine/0.5% BSA and washed 3 times with 25 mM NaCl, 10 mM TrisHCl, 1 mM MgSO$_4$, 0.5 mM EDTA, 0.03% CHAPS, pH 7.4. The filter is then dried and counted on the Betaplate liquid scintillation counter. The recombinant IL-8 Rα, or Type I, receptor is also referred to herein as the non-permissive receptor and the recombinant IL-8 Rβ, or Type II, receptor is referred to as the permissive receptor.

Representative compounds of Formula (I), Examples 1 to 8, have been found to have positive inhibitory activity of <30 μmg in this assay.

Chemotaxis Assay

The in vitro inhibitory properties of these compounds are determined in the neutrophil chemotaxis assay as described in Current Protocols in Immunology, vol. I, Suppl 1, Unit 6.12.3., whose disclosure is incorporated herein by reference in its entirety. Neutrophils where isolated from human blood as described in Current Protocols in Immunology Vol. I, Suppl. 1 Unit 7.23.1, whose disclosure is incorporated herein by reference in its entirety. The chemoattractants IL-8, GRO-α, GRO-β, GRO-65 and NAP-2 are placed in the bottom chamber of a 48 multiwell chamber (Neuro Probe, Cabin John, MD) at a concentration between 0.1 and 100 nM. The two chambers are separated by a 5 μm polycarbonate filter. When compounds of this invention are tested, they are mixed with the cells (0.001–1000 nM) just prior to the addition of the cells to the upper chamber. Incubation is allowed to proceed for between about 45 and 90 min. at about 37° C. in a humidified incubator with 5% CO$_2$. At the end of the incubation period, the polycarbonate membrane is removed and the top side washed, the membrane then stained using the Diff Quick staining protocol (Baxter Products, McGaw Park, Ill., USA). Cells which have chemotaxed to the chemokine are visually counted using a microscope. Generally, four fields are counted for each sample, these numbers are averaged to give the average number of cells which had migrated. Each sample is tested in triplicate and each compound repeated at least four times. To certain cells (positive control cells) no compound is added, these cells represent the maximum chemotactic response of the cells. In the case where a negative control (unstimulated) is desired, no chemokine is added to the bottom chamber. The difference between the positive control and the negative control represents the chemotactic activity of the cells.

Elastase Release Assay

The compounds of this invention are tested for their ability to prevent Elastase release from human neutrophils. Neutrophils are isolated from human blood as described in Current Protocols in Immunology Vol. 1, Suppl 1 Unit 7.23.1. PMNs $0.88 \times 10^6$ cells suspended in Ringer's Solution (NaCl 118, KCl 4.56, NaHCO3 25, KH2PO4 1.03, Glucose 11.1, HEPES 5 mM, pH 7.4) are placed in each well of a 96 well plate in a volume of 50 ul. To this plate is added the test compound (0.001–1000 nM) in a volume of 50 ul, Cytochalasin B in a volume of 50 ul (20 ug/ml) and Ringers buffer in a volume of 50 ul. These cells are allowed to warm (37° C., 5% CO2, 95% RH) for 5 min. before IL-8, GROα, GROβ, GROγ or NAP-2 at a final concentration of 0.01–1000 nM was added. The reaction is allowed to proceed for 45 min. before the 96 well plate is centrifuged (800×g 5 min.) and 100 ul of the supernatant removed. This supernatant is added to a second 96 well plate followed by an artificial elastase substrate (MeOSuc-Ala-Ala-Pro-Val-AMC, Nova Biochem, La Jolla, Calif.) to a final concentration of 6 ug/ml dissolved in phosphate buffered saline. Immediately, the plate is placed in a fluorescent 96 well plate reader (Cytofluor 2350, Millipore, Bedford, Mass.) and data collected at 3 min. intervals according to the method of Nakajima et al J. Biol Chem 254 4027 (1979). The amount of Elastase released from the PMNs is calculated by measuring the rate of MeOSuc-Ala-Ala-Pro-Val-AMC degradation.

TNF-α in Traumatic Brain Injury Assay

This assay provides for examination of the expression of tumor necrosis factor mRNA in specific brain regions which follow experimentally induced lateral fluid-percussion percussion traumatic brain injury (TBI) in rats. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma. A suitable assay may be found in WO 97/35856 or WO 97/49286 whose disclosures are incorporated herein by reference.

CNS Injury model for IL-β mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 or WO 97/49286 whose disclosures are incorporated herein by reference.

In vivo—Athereosclerosis Assay

In vivo models for measuring atherosclerosis in mice is based on the assay of Paigen et al with small modifications as described below. See Paigen B, Morrow A, Holmes P A, Mitchell D, Williams R A. Quantitative assessment of atherosclerotic lesions in mice. *Atherosclerosis* 68: 231–240 (1987); and Groot P H E, van Vlijmen B J M, Benson G M, Hofker M H, Schiffelers R, Vidgeon-Hart M, Havekes L M. Quantitative assessment of aortic atherosclerosis in APOE*3 Leiden transgenic mice and its relationship to serum cholesterol exposure. *Arterioscler Thromb Vasc Biol.* 16:926–933 (1996).

Sectioning and Staining of the Aortic Sinus

Cross-sections of the aortic root are taken as has been described previously (1,2). Briefly, the hearts are bisected just below the level of the atria and the base of the heart plus aortic root are taken for analysis. After equilibrating the tissue in OCT compound overnight the hearts are immersed in OCT compound on a cryostat chuck (Bright Instrument Company Ltd., UK) with the aorta facing the chuck. The tissue is frozen by surrounding the chuck with dry ice. The hearts are then sectioned perpendicular to the axis of the aorta, starting within the heart and working in the direction of the aorta. Once the aortic root has been identified by the appearance of the three valve leaflets, alternate 10 mm sections are taken and mounted on gelatinized slides. Sections are air dried for 1 hour and subsequently rinsed briefly in 60% isopropyl alcohol. The sections are stained with Oil Red O, counterstained with Mayer's haematoxylin, cover slipped using glycerol gelatin and sealed with nail varnish.

Quantification of Atherosclerosis in the Aortic Root

Ten alternate sections of the aortic root are imaged using an Olympus BH-2 microscope equipped with an 4× objective and a video camera (Hitachi, HV-C10). Twenty-four bit colour images are acquired and analyzed using a PC (Datacell Pentium P5-133, Datacell, Berks, U.K.) fitted with a framegrabbing board (Snapper, Active Imaging Ltd, Berks, U.K.) and running Optimas software (version 5.1, Optimas Corp., Wash., U.S.A.). The images are captured under identical lighting, microscope, camera and PC conditions. Quantification of the atherosclerotic lesion areas is performed by drawing around the lesions by hand using the Optimas software. Colour thresholds are set that quantify the areas that are stained red within the lesions. Absolute values for the cross-sectional areas of the lesions and the areas stained red are obtained by calibrating the software using an image of the grid on a haemocytometer slide.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula:

(I)

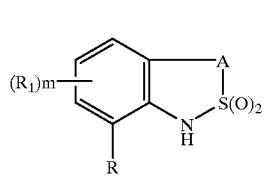

wherein

R is —NH—C(X)—NH—$(CR_{13}R_{14})_v$—Z;

Z is W, optionally substituted heteroaryl, optionally substituted $C_{5-8}$ cycloalkyl, optionally substituted $C_{1-10}$ alkyl, optionally substituted $C_{2-10}$ alkenyl, or an optionally substituted $C_{2-10}$ alkynyl;

X is =O, or =S;

A is $CR_{20}R_{21}$;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)qS(O)_tR_4$, hydroxy; hydroxy $C_{1-4}$alkyl; aryl; aryl $C_{1-4}$ alkyl; aryloxy; aryl$C_{1-4}$ alkyloxy; heteroaryl; heteroarylalkyl; heterocyclic; heterocyclic$C_{1-4}$alkyl; heteroaryl$C_{1-4}$ alkyloxy; aryl$C_{2-10}$ alkenyl; heteroaryl$C_{2-10}$ alkenyl; heterocyclic$C_{2-10}$ alkenyl; $(CR_8R_8)qNR_4R_5$; $C_{2-10}$alkenylC(O)NR$_4R_5$; $(CR_8R_8)qC(O)NR_4R_5$; $(CR_8R_8)qC(O)NR_4R_{10}$; S(O)$_3$H; S(O)$_3R_8$; $(CR_8R_8)qC(O)R_{11}$; $C_{2-10}$ alkenylC(O)R$_{11}$; $C_{2-10}$alkenylC(O)OR$_{11}$; $(CR_8R_8)qC(O)OR_{11}$; $(CR_8R_8)qC(O)OR_{12}$; $(CR_8R_8)qOC(O)R_{11}$; $(CR_8R_8)qNR_4C(O)R_{11}$; $(CR_8R_8)qC(NR_4)$ NR$_4R_5$; $(CR_8R_8)qNR_4C(NR_5)R_{11}$; $(CR_8R_8)qNHS(O)_2R_{17}$; and $(CR_8R_8)qS(O)_2NR_4R_5$; or two $R_1$ moieties together may form O—(CH$_2$)$_s$O or a 5 to 6 membered saturated or unsaturated ring, and wherein the aryl, heteroaryl, and heterocyclic containing rings may be optionally substituted;

n is an integer having a value of 1 to 3;

m is an integer having a value of 1 or 3;

q is 0, or an integer having a value of 1 to 10;

t is 0, or an integer having a value of 1 or 2;

s is an integer having a value of 1 to 3;

v is 0, or an integer having a value of 1 to 4;

$R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, or heterocyclic $C_{1-4}$ alkyl, or $R_4$ and $R_5$ together with the nitrogen to which they are attached form a 5 to 7 member ring which may optionally comprise an additional heteroatom selected from oxygen, nitrogen and sulfur;

Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)qS(O)_tR_4$; hydroxy; hydroxy$C_{1-4}$alkyl; aryl; aryl $C_{1-4}$ alkyl; aryloxy; aryl$C_{1-4}$ alkyloxy; heteroaryl; heteroarylalkyl; heteroaryl $C_{1-4}$ alkyloxy; heterocyclic, heterocyclic$C_{1-4}$alkyl; aryl $C_{2-10}$ alkenyl; heteroaryl$C_{2-10}$ alkenyl; heterocyclic$C_{2-10}$alkenyl; $(CR_8R_8)qNR_4R_5$; $C_{2-10}$alkenylC(O)NR$_4R_5$; $(CR_8R_8)qC(O)NR_4R_5$; $(CR_8R_8)qC(O)NR_4R_{10}$; S(O)$_3$H; S(O)$_3R_8$; $(CR_8R_8)qC(O)R_{11}$; $C_{2-10}$ alkenylC(O)R$_{11}$; $C_{2-10}$alkenylC(O)OR$_{11}$; $(CR_8R_8)qC(O)OR_{11}$; $(CR_8R_8)qC(O)OR_{12}$; $(CR_8R_8)qOC(O)R_{11}$; $(CR_8R_8)qNR_4C(O)R_{11}$; $(CR_8R_8)qC(NR_4)$ NR$_4R_5$; $(CR_8R_8)qNR_4C(NR_5)R_{11}$; $(CR_8R_8)qNHS(O)_2R_{18}$; and $(CR_8R_8)qS(O)_2NR_4R_5$; or two Y moieties together may form O—(CH$_2$)$_s$O or a 5 to 6 membered saturated or unsaturated ring, and wherein the aryl, heteroaryl, and heterocyclic containing rings, may be optionally substituted;

$R_6$ and $R_7$ are independently hydrogen or a $C_{1-4}$ alkyl group, or $R_6$ and $R_7$ together with the nitrogen to which they are attached form a 5 to 7 member ring which ring may optionally contain an additional heteroatom which heteroatom is selected from oxygen, nitrogen and sulfur;

$R_8$ is independently hydrogen or $C_{1-4}$ alkyl;

$R_{10}$ is $C_{1-10}$ alkyl $C(O)_2R_8$;

$R_{11}$ is hydrogen, $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$alkyl;

$R_{12}$ is hydrogen, $C_{1-10}$ alkyl, optionally substituted aryl or optionally substituted arylalkyl;

$R_{13}$ and $R_{14}$ are independently hydrogen, optionally substituted $C_{1-4}$ alkyl, or one of $R_{13}$ and $R_{14}$ may be an optionally substituted aryl;

$R_{15}$ and $R_{16}$ are independently hydrogen, or an optionally substituted $C_{1-4}$ alkyl;

$R_{17}$ is $C_{1-4}$alkyl, arylalkyl, heteroaryl, heteroaryl$C_{1-4}$alkyl, heterocyclic, or heterocyclic$C_{1-4}$alkyl, wherein the aryl, heteroaryl and heterocyclic rings may all be optionally substituted;

$R_{18}$ is NR$_6R_7$, alkyl, aryl$C_{1-4}$ alkyl, aryl$C_{2-4}$alkenyl, heteroaryl, heteroaryl-$C_{1-4}$alkyl, heteroaryl$C_{2-4}$ alkenyl, heterocyclic, or heterocyclic$C_{1-4}$ alkyl, wherein the aryl, heteroaryl and heterocyclic rings may all be optionally substituted;

$R_{20}$ and $R_{21}$ are independently halogen, cyano, halosubstituted $C_{1-10}$alkyl, $C_{3-10}$alkyl, aryl, aryl $C_{1-4}$ alkyl, heteroaryl; heteroarylalkyl, heterocyclic, heterocyclic $C_{1-4}$alkyl, $(CR_8R_8)qOR_4$, $(CR_8R_8)qC(O)R_{11}$, $(CR_8R_8)qC(O)OR_{11}$, $(CR_8 R_8)qC(O)OR_{12}$; $(CR_8R_8)qOC(O)R_{11}$, $(CR_8R_8)qNR_4R_5$, $(CR_8R_8)qNR_4C(O)R_{11}$, or $(CR_8R_8)qC(O)NR_4R_5$, or together $R_{20}$ and $R_{21}$ may form =R$_{22}$; and wherein the aryl, heteroaryl, and heterocyclic containing rings may be optionally substituted;

$R_{22}$ is a $C_{1-4}$ alkyl, aryl $C_{1-4}$ alkyl, heteroarylalkyl, or heterocyclic $C_{1-4}$alkyl, such that attachment is through the alkyl moiety, where present, and wherein all of these moieties may be optionally substituted;

W is

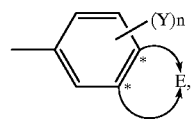

or

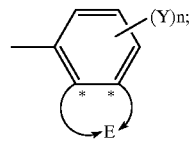

the E containing ring is selected from

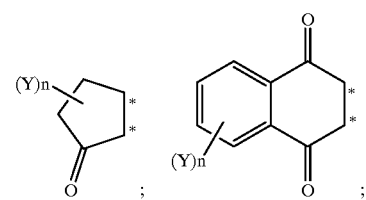

-continued

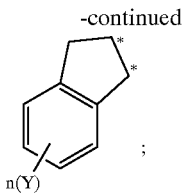

and

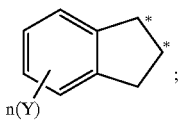

the asterix * denoting point of attachment of the ring; or a pharmaceutically acceptable salt thereof.

2. The compound according to claim 1 wherein at least one of $R_{20}$ and $R_{21}$ is an optionally substituted alkyl, halogen, $(CR_8R_8)qC(O)NR_4R_5$, optionally substituted heteroaryl, or an optionally substituted heterocyclic, or $R_{20}$ and $R_{21}$ together are a methylene.

3. The compound according to claim 1 wherein X is oxygen.

4. The compound according to claim 1 wherein $R_1$ is halogen, cyano, nitro, CF3, $C(O)NR_4R_5$, alkenyl $C(O)NR_4R_5$, $C(O)NR_4R_{10}$, alkenyl $C(O)OR_{11}$, heteroaryl, heteroarylalkyl, heteroaryl alkenyl, or $(CR_8R_8)qS(O)2NR_4R_5$.

5. The compound according to claim 1 wherein Z is W.

6. The compound according to claim 5 wherein Y is halogen, $C_{1-4}$ alkoxy, optionally substituted aryl, optionally substituted arylalkoxy, methylene dioxy, $NR_4R_5$, thio$C_{1-4}$alkyl, thioaryl, halosubstituted alkoxy, optionally substituted $C_{1-4}$alkyl, or hydroxy substituted alkyl.

7. The compound according to claim 4 wherein Z is an optionally substituted heteroaryl.

8. The compound according to claim 1 which is:

[N-[(1,3)-Dihydro-2,2-dioxo-3methyl-4-chloro-2,1-benzisothiazo)-7-yl]-N'-[2-bromophenyl]urea];
N-[(1,3)-Dihydro-2,2-dioxo-3-propyl-4-chloro-2,1-benzisothiazo)-7-yl]-N'-[2-bromophenyl]urea;
N-[(1-hydro-2,2-dioxo-3,3-dimethyl-4-chloro-2,1-benzisothiazo)-7-yl]-N'-[2-bromophenyl]urea;
N-[(1,3)-Dihydro-2,2-dioxo-3-fluoro-4-chloro-2,1-benzisothiazo)-7-yl]-N'-[2-bromophenyl]urea;
N-[(1,3)-Dihydro-2,2-dioxo-3-methylamide-4-chloro-2,1-benzisothiazo)-7-yl]-N'-[2-bromophenyl]urea;
N-[(1,3)-Dihydro-2,2-dioxo-3-methyl-3-methylamide-4-chloro-2,1-benzisothiazo)-7-yl]-N'-[2-bromophenyl]urea;
N-[(1,3)-Dihydro-2,2-dioxo-3-methylene-4-chloro-2,1-benzisothiazo)-7-yl]-N'-[2-bromophenyl]urea; or
N-[( 1,3)-Dihydro-2,2-dioxo-3-(benzothiazol-2-yl)-4-chloro-2,1-benzisothiazo)-7-yl]-N'-[2-bromophenyl]urea;

or a pharmaceutically acceptable salt thereof.

9. The pharmaceutical composition comprising an effective amount of a compound according to, claim 1 and a pharmaceutically acceptable carrier or diluent.

10. A method of treating a chemokine mediated disease in a mammal in need thereof, wherein the chemokine binds to an IL-8 a or b receptor, which method comprises administering to said mammal an effective amount of a compound according to claim 1.

11. The method according to claim 10 wherein the chemokine mediated disease is selected from psoriasis, atopic dermatitis, asthma, chronic obstructive pulmonary disease, adult respiratory distress syndrome, arthritis, inflammatory bowel disease, Crohn's disease, ulcerative colitis, septic shock, endotoxic shock, gram negative sepsis, toxic shock syndrome, stroke, cardiac and renal reperfusion injury, glomerulonephritis, thrombosis, atherosclerosis, bone resorption diseases, Alzheimer's disease, graft vs. host reaction, or allograft rejections.

12. A process for producing a compound of Formula (I) as defined in claim 1, which process comprises a) reacting a compound of the formula:

(II)

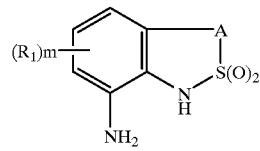

with a compound of the formula:

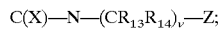

$C(X)—N—(CR_{13}R_{14})_v—Z$;

wherein A, $R_1$, m, X, $R_{13}$, $R_{14}$, v and Z are as defined in Formula (I) to yield a compound of Formula (I); and thereafter if necessary, deprotecting, or converting a precursor of $R_1$, A, or Z to a group $R_1$, A or Z.

13. A process for making a compound of the formula:

(II)

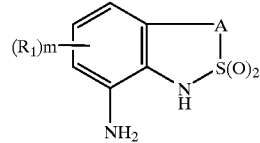

wherein

A is $CR_{20}R_{21}$;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)qS(O)_tR_4$, hydroxy; hydroxy $C_{1-4}$alkyl; aryl; aryl $C_{1-4}$ alkyl; aryloxy; aryl$C_{1-4}$ alkyloxy; heteroaryl; heteroarylalkyl; heterocyclic; heterocyclic$C_{1-4}$alkyl; heteroaryl$C_{1-4}$ alkyloxy; aryl$C_{2-10}$ alkenyl; heteroaryl$C_{2-10}$ alkenyl; heterocyclic$C_{2-10}$alkenyl; $(CR_8R_8)qNR_4R_5$; $C_{2-10}$alkenylC(O)NR_4R_5$; $(CR_8R_8)qC(O)NR_4R_5$; $(CR_8R_8)qC(O)NR_{10}$; $S(O)_3H$; $S(O)_3R_8$; $(CR_8R_8)qC(O)R_{11}$; $C_{2-10}$ alkenylC(O)R_{11}$; $C_{2-10}$alkenylC(O)OR_{11}$; $(CR_8R_8)qC(O)OR_{11}$; $(CR_8R_8)qC(O)OR_{12}$; $(CR_8R_8)qOC(O)R_{11}$; $(CR_8R_8)qNR_4C(O)R_{11}$; $(CR_8R_8)qC(NR_4)NR_4R_5$; $(CR_8R_8)qNR_4C(NR_5)R_{11}$; $(CR_8R_8)qNHS(O)_2R_{17}$; $(CR_8R_8)qS(O)_2NR_4R_5$; or two $R_1$ moieties together may form $O—(CH_2)_sO$ or a 5 to 6 membered saturated or unsaturated ring, and wherein the aryl, heteroaryl, and heterocyclic containing rings may be optionally substituted;

m is an integer having a value 1 or 3, which process comprises reducing a compound of the formula:

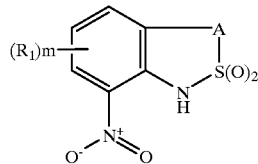

(III)

wherein A, R$_1$, and m are as under suitable reducing conditions to yield a compound of Formula (II).

14. A process for producing a compound of Formula (I), as defined in claim 1 which process comprises reacting a compound of the formula:

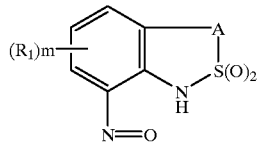

(IV)

wherein A, R$_1$, and m are as defined for Formula (I); with a compound of the formula:

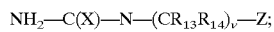

NH$_2$—C(X)—N—(CR$_{13}$R$_{14}$)$_v$—Z;

wherein X, R$_{13}$, R$_{14}$, v and Z are as defined in Formula (I), to yield a compound of Formula (I), and thereafter if necessary, deprotecting, or converting a precursor of R$_1$, A, or Z to a group R$_1$, A or Z.

* * * * *